(12) United States Patent
Johansen

(10) Patent No.: US 9,132,251 B2
(45) Date of Patent: Sep. 15, 2015

(54) MEDICAL BREATHING MASK

(75) Inventor: Troels Johansen, Arahus C (DK)

(73) Assignee: BALANCAIR APS, Aarhus C (DK)

( * ) Notice: Subject to any disclaimer, the term of this patent is extended or adjusted under 35 U.S.C. 154(b) by 527 days.

(21) Appl. No.: 13/445,049

(22) Filed: Apr. 12, 2012

(65) Prior Publication Data

US 2012/0240935 A1  Sep. 27, 2012

Related U.S. Application Data

(63) Continuation-in-part of application No. PCT/DK2010/050270, filed on Oct. 14, 2010.

(30) Foreign Application Priority Data

Oct. 14, 2009  (DK) .................................. 2009 01122

(51) Int. Cl.

| | |
|---|---|
| *A61M 16/00* | (2006.01) |
| *A62B 7/10* | (2006.01) |
| *A62B 23/02* | (2006.01) |
| *A62B 18/02* | (2006.01) |
| *A61M 16/06* | (2006.01) |
| *A61M 16/08* | (2006.01) |
| *A61M 16/20* | (2006.01) |

(52) U.S. Cl.
CPC ........... *A61M 16/0045* (2013.01); *A61M 16/06* (2013.01); *A61M 16/0078* (2013.01); *A61M 16/0808* (2013.01); *A61M 16/208* (2013.01); *A61M 2205/18* (2013.01); *A61M 2205/502* (2013.01); *A61M 2205/7536* (2013.01); *A61M 2230/432* (2013.01)

(58) Field of Classification Search
USPC ............. 128/205.25, 205.28, 205.13, 205.24, 128/201.25, 205.12, 206.21, 206.22, 128/205.27, 206.28
See application file for complete search history.

(56) References Cited

U.S. PATENT DOCUMENTS

| | | | |
|---|---|---|---|
| 3,513,843 A | 5/1970 | Exler | |
| 4,141,703 A * | 2/1979 | Mulchi | ........................... 96/132 |
| 4,192,301 A | 3/1980 | Hardwick | |
| 4,275,722 A | 6/1981 | Sorensen | |
| 4,361,146 A * | 11/1982 | Woicke | ..................... 128/206.12 |
| 4,440,163 A * | 4/1984 | Spergel | ..................... 128/205.13 |

(Continued)

FOREIGN PATENT DOCUMENTS

| | | |
|---|---|---|
| CN | 2655928 Y | 11/2004 |
| CN | 1723074 A | 1/2006 |

(Continued)

OTHER PUBLICATIONS

Office Action issued in corresponding Japanese Application No. 2012-533484 dated Aug. 5, 2014.
Office Action issued in corresponding Chinese Application No. 201080056229.7 dated May 5, 2014.

*Primary Examiner* — Kristen Matter
(74) *Attorney, Agent, or Firm* — Pearne & Gordon LLP

(57) ABSTRACT

A facial breathing mask suitably for regulating the carbon dioxide concentration in the inspired air, the facial mask comprising an air chamber with an opening through which a user can breathe. At least a part of the air chamber is flexible and/or collapsible and comprises one or more of semi-permeable membranes separating the air chamber and a surrounding atmosphere.
In use, the invention can raise the carbon dioxide tension in the inspired air and/or influence the depth and rate of breathing of the user.

14 Claims, 5 Drawing Sheets

(56) References Cited

U.S. PATENT DOCUMENTS

| | | | |
|---|---|---|---|
| 4,508,116 A | | 4/1985 | Duncan et al. |
| 4,964,405 A | * | 10/1990 | Arnoth .................... 128/205.17 |
| 5,154,167 A | * | 10/1992 | Hepburn ................. 128/200.24 |
| 5,647,345 A | | 7/1997 | Saul |
| 2003/0024533 A1 | * | 2/2003 | Sniadach ................ 128/205.25 |
| 2006/0144399 A1 | * | 7/2006 | Davidowski et al. .... 128/205.12 |
| 2008/0245370 A1 | * | 10/2008 | Kobziar et al. .......... 128/206.21 |
| 2011/0162651 A1 | * | 7/2011 | Drew et al. ............. 128/205.25 |
| 2012/0103339 A1 | * | 5/2012 | Koehler ................. 128/206.14 |

FOREIGN PATENT DOCUMENTS

| | | |
|---|---|---|
| DE | 19912337 C1 | 8/2000 |
| GB | 2378904 A | 2/2003 |
| JP | 2001-505813 A | 5/2001 |
| JP | 2008-526275 A | 7/2008 |
| UA | 74957 C2 | 12/2005 |
| WO | 93/23102 A1 | 11/1993 |
| WO | 97/28837 A1 | 8/1997 |

\* cited by examiner

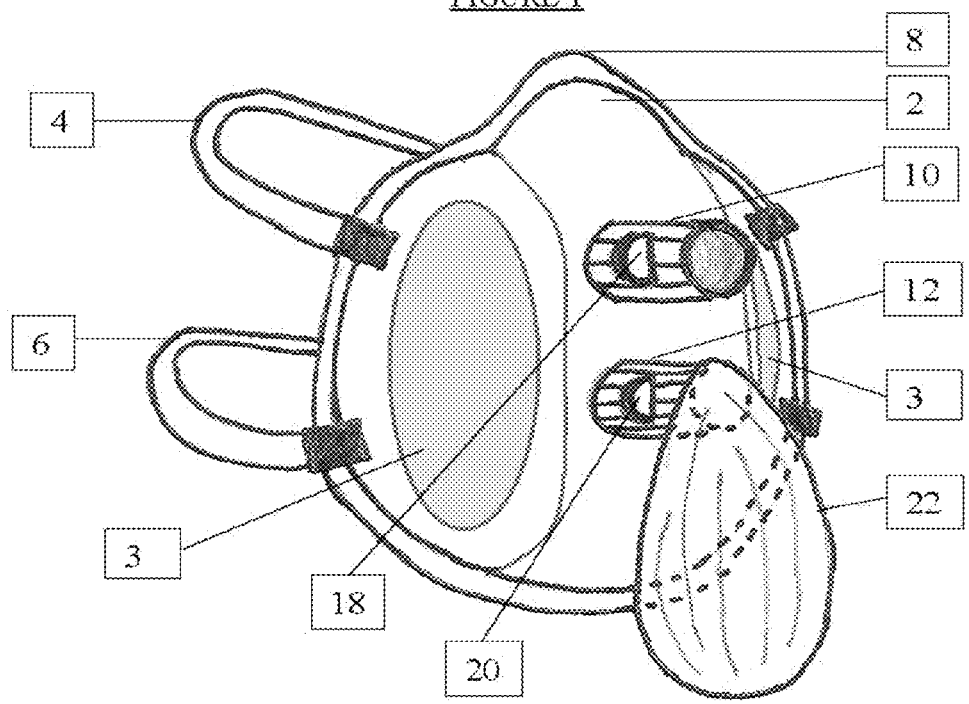
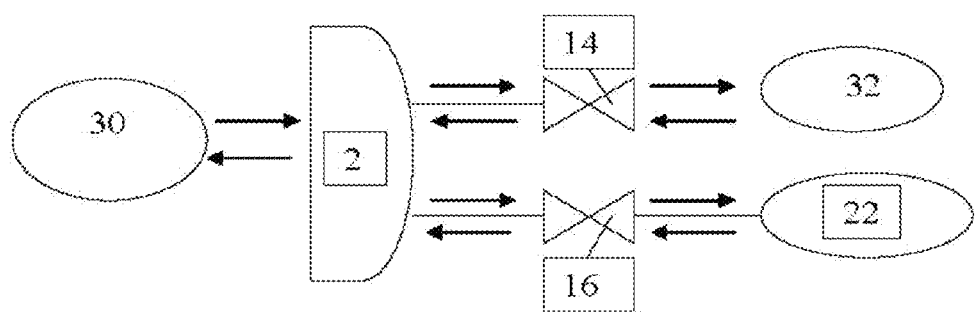

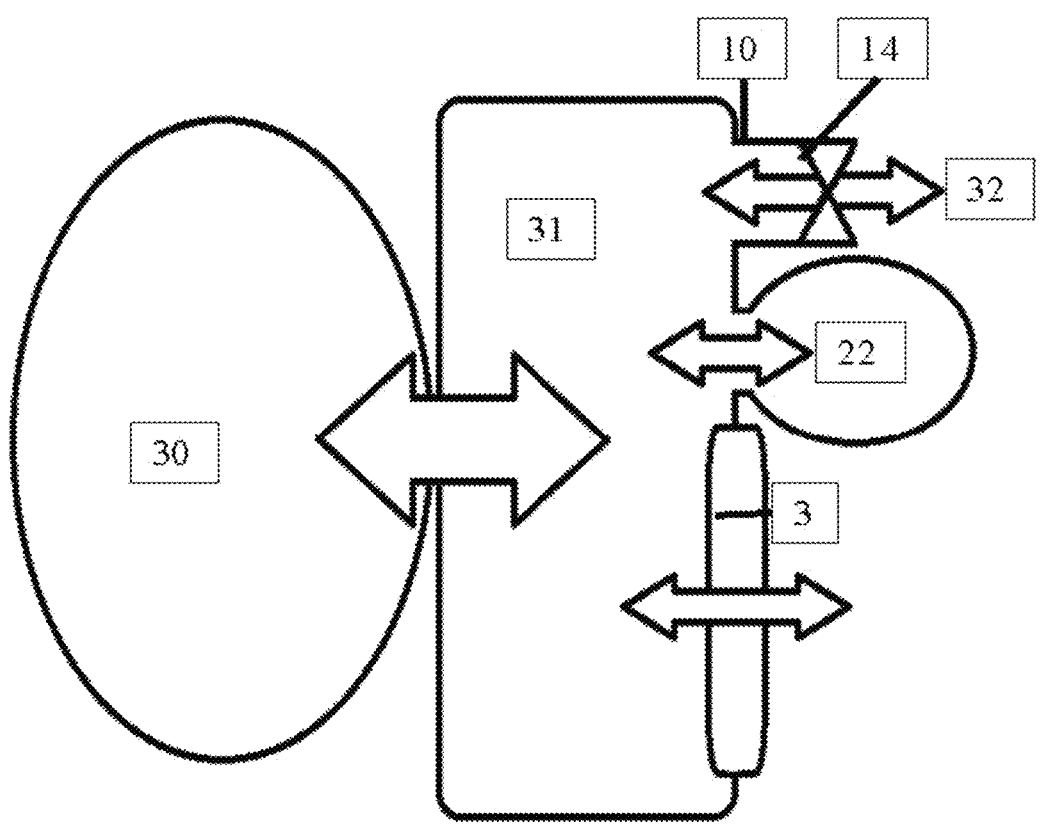

MEDICAL BREATHING MASK

CROSS-REFERENCE TO RELATED APPLICATIONS

This application is a continuation-in-part of patent application number PCT/DK2010/050270 filed on Oct. 14, 2010.

BACKGROUND OF THE INVENTION

In a range of different common medical disorders (among them panic anxiety, epilepsy, febrile seizures, asthma, idiopathic dyspnea, and certain heart conditions) patients are often found to have a lowered carbon dioxide tension in the body. This condition is called hypocapnia and is in almost every case caused by hyperventilation, meaning that the patient is—on average—breathing in excess of metabolic requirements, a reaction that may be initially prompted by emotional or physical stress. Hyper-ventilatory breathing patterns may be characterized by either sudden hyperventilation attacks, slight chronic overbreathing, oscillations between over—and underbreathing, and/or a generally normal breathing rate interspersed with frequent sighs and/or deep breaths. In the case of sudden increases in the ventilatory flow, one of the most important consequences is an almost instantaneous drop in the arterial carbon dioxide tension, followed rapidly by a rise in the pH value of the blood (alkalosis), in turn affecting the blood flow to the brain, the oxygen delivery to the cells, the excitability of the nervous systems, the tension of the smooth muscles, as well as other physiological parameters. These changes can lead to a range of symptoms depending on the individual patient, including dyspnea, chest pains, panic, tingling/numbness in the extremities, cramps, fainting, seizures etc. Often, these symptoms will be ascribed to other afflictions, such as a heart condition, asthma, epilepsy, panic anxiety etc., where in fact the symptoms are induced by hyperventilation.

If hypocapnia is sustained over days or weeks, the kidneys will gradually compensate for the rise in the pH value. This process is called compensatory metabolic acidosis and will partially (but rarely completely) restore the normal blood pH value. Many other parameters, among them arterial $CO_2$ tension, bicarbonate concentration and other ion concentrations, will remain at abnormal levels, however. In particular, the reduction in the bicarbonate concentration will impair the acid/base buffering capacity of the body.

Long-term hyperventilation may also have a self-sustaining effect. Under normal circumstances, the alkalosis induced by hyperventilation will diminish the chemoreceptor output signal, thereby lowering the ventilation, i.e. constraining hyperventilation. However, this physiological "brake" is weakened by the compensatory metabolic acidemia which develops in long term (days or weeks) hyperventilation. It is possible that this can lead to hyperventilation becoming self-sustaining.

Furthermore, the theory has been proposed that hyperventilation and hypocapnia can be due to a heightened carbon dioxide sensitivity of the chemoreceptors and/or the respiratory center in the brain, possibly as a result of long term hyperventilation inducing a change in body homeostasis. This would indicate a change in the ventilatory "set point" which can be hard to reverse.

Referring to the prior art, a rebreathing mask is disclosed in PCT patent application WO97/28837, consisting of a rim section to which is attached a bag made of a material impenetrable to the passage of air. U.S. Pat. No. 4,508,116 discloses a rebreathing apparatus, in which the user breathes through an elongated air pathway from the atmosphere to the mouthpiece, achieving an accumulation of carbon dioxide. U.S. Pat. No. 3,513,843 discloses a respiratory device for regulating the carbon dioxide level of inhalation consisting of a nose-mouth mask connected to an inflatable sack; of readily variable size to adjust the same to the breathing capacity of the user, said sack having an adjustable two-way flow breather valve and a one-way outlet valve. U.S. Pat. No. 4,275,722 discloses a breathing apparatus in which a mouthpiece and a valve device between the mouthpiece and the chambers for directing the air flow are provided, and an adjustable mechanism is used to vary the amount of exhaled air which is mixed with ambient air to be rebreathed. U.S. Pat. No. 5,647,345 discloses a breathing apparatus comprising a mixing chamber with a breathing port and at least one vent port. UK patent number 2378904 discloses a breathing apparatus comprising an enclosed bag which is impermeable to moisture, the bag being fitted with a mouthpiece adapted to be held between the user's lips, the mouthpiece being in fluid communication with the interior of the bag, and wherein a filter is interposed between said mouthpiece and said bag and wherein there is provided a fresh air inlet between said mouthpiece and said filter. U.S. Pat. No. 4,192,301 discloses a breathing apparatus consisting of a disposable, flexible polymer bag which attaches to a nose/mouth mask and an air control valve located between the mask and the disposable bag which adjusts the ratio of rebreathed to fresh air through a fresh air inlet. The fresh air inlet has a check valve preventing exhaling air therethrough and a pressure relief valve may be provided to release rebreathed air when the polymer bag becomes filled. Ukranian patent number UA 74957 C2 discloses a breathing mask fitted with an expandable bag and two adjustable valves for allowing fresh air to flow into the mask volume. German patent number DE 19912337 discloses a breathing mask fitted with a tube, connecting the mask to an expandable bag; at the connection between the tube and mask, an opening of adjustable size is fitted.

BRIEF SUMMARY OF THE INVENTION

The aim of the present invention is to provide a facial mask suitable for help in reestablishing healthy physiological parameters in a patient, such as pH value, carbon dioxide tension, bicarbonate and/or other ion concentrations, by raising the carbon dioxide tension in the inspired air and/or by affecting the depth and rate of breathing. This is met by the medical breathing mask of the invention. The medical breathing mask of the invention can accordingly be used by a patient for reestablishing healthy physiological parameter(s). Use of the medical breathing mask of the invention has shown to result in raising the carbon dioxide tension in the air inspired by the patient through a partial rebreathing of expired air, with a relatively small decrease in the bodily oxygen level, without using a supply of stored oxygen or carbon dioxide. By increasing the inspired CO2 concentration, it has been found that the respiratory alkalosis induced by hyperventilation will be reduced or even negated, which typically will lead to a significant reduction of the symptoms of acute hyperventilation.

In chronic hyperventilation, it is possible that a lowered CO2 "set point" can be reversed by inducing normocapnia (i.e. a normal CO2 level) over longer periods of time. An effect of such a treatment would be to gradually counteract the compensatory metabolic acidemia (thereby reestablishing the normal "$CO_2$ brake" on hyperventilation), as well as possibly lowering the carbon dioxide sensitivity of the body.

One embodiment of the medical breathing mask of the invention has been shown in practice to be well suited for this purpose.

The invention can also be used to raise the carbon dioxide tension in the body above the normal level, should it be desired for any reason. Also, the invention can be used to lower the pH value of the blood below the normal level, should this be desired (as might be the case in hyperventilation, migraine, epilepsy, febrile seizures, critical illness and birth asphyxia, among others). Additionally, the invention can be used to change the depth and/or rate of breathing from its normal level, should this be desired.

In one embodiment, the invention has the form of a breathing mask with a main breathing port (the primary opening) which can be arranged to fit tightly around the nose and mouth of the user and which allows the wearer to breathe through the mask. A number of semi-permeable membranes in the wall of the nose/mouth-enclosing part of the mask (the primary air chamber) provide a means of air exchange between the primary air chamber and the surrounding atmosphere. A semi-permeable membrane is defined as a material or membrane that offers a resistance to the flow of gas through it, and/or a material through which one gas component (e.g. oxygen, carbon dioxide, water, nitrogen etc.) travels faster than another gas component. In this embodiment, the primary air chamber is furthermore connected to a bag which is expandable (the flexible air chamber), meaning that it can expand and contract according to the pressure level inside. This bag can be made from both an elastic or non-elastic material. In one embodiment of the invention, the surface of the primary air chamber is fitted with an additional opening (the fresh air valve) which provides an additional mode of gas transport between the primary air chamber and the surrounding atmosphere In experiments with this embodiment of the invention, it was found that it was possible to adjust the valves in such a way that the average carbon dioxide concentration in the inspired gas was roughly 2%, with an average oxygen concentration in the inspired gas of roughly 17%. At these values of carbon dioxide and oxygen concentrations, no adverse effect or discomfort was experienced by the user (further test data are presented in the in the paragraph "Examples", below).

In one embodiment of the invention, one or more of the openings of the mask are fitted with adjustable valves which can be of any type (for example ball or butterfly valves), thereby for example allowing the user of the mask or someone else to vary the flow rate of air between the primary air chamber and the atmosphere, as well as the flow rate of air between the primary air chamber and the flexible air chamber.

By adjusting the flow diameter of the valve between the primary air chamber and the surrounding atmosphere (the fresh air valve), the flow of fresh air into the primary air chamber can be regulated, as well as the flow of expired gas from the primary air chamber to the atmosphere. Decreasing the flow diameter in this opening will mean that the composition of the inspired gas will become richer in previously expired air and poorer in fresh air, thereby giving the inspired air a higher content of carbon dioxide but a lower content of oxygen. This valve thereby makes it possible to adjust the concentrations of carbon dioxide, oxygen and water vapor in the inspired air. By adjusting the flow diameter of the valve between the primary air chamber and the flexible air chamber (the bag valve), the amplitude of the pressure fluctuation inside the primary air chamber (a pressure fluctuation caused by the act of breathing) is affected, in such a way that a small flow diameter in the bag valve will produce a greater pressure fluctuation in the primary air chamber than that produced by having a larger flow diameter in the bag valve. In other words, the larger the flow diameter in the bag valve, the better the pressure buffering (and the more constant the air pressure) in the primary air chamber will be.

Experiments with this embodiment of the mask have shown that by decreasing the bag valve flow diameter, the tidal volume of each breath will be heightened (i.e. deeper breaths), whereas the time between breaths will be longer (i.e. a lower breathing frequency). Furthermore, by regulating the flow diameter in the bag valve, the amount of carbon dioxide which is rebreathed from the flexible air chamber can be adjusted.

In one embodiment of the invention, the described valves are self-regulating, automatically adjusting the flow diameter through them according to (for example) the rate of flow through them and/or the level of the pressures on either side of the valve, one such possible type of valve being a one-way flap or check valve. In one embodiment of the invention, the flexible air chamber is fitted directly on the primary chamber, with no pipe or other constriction between the two chambers.

A facial breathing mask comprises a primary air chamber which is made from a flexible material in such a way that the volume of said chamber is able to vary according to the mass of air inside said chamber.

In one embodiment of the invention, the walls of the flexible air chamber are partially or entirely made from a semi-permeable material. In one embodiment of the invention, the semi-permeable membranes can be porous in nature, whereas in another embodiment they can be non-porous in nature. In the case of some porous membranes and materials, the diffusion rate of carbon dioxide through the membrane will be lower than the diffusion speed of oxygen through the same membrane (as by Graham's Law of Diffusion), in effect making it harder for carbon dioxide to diffuse out the mask volume than for oxygen to diffuse into the mask volume, thereby making possible a comparatively larger oxygen concentration at a given carbon dioxide concentration in the mask volume. In one embodiment of the invention, one or more of the semi-permeable membranes are of a hydrophobic nature, meaning that liquid water is not absorbed or transported into the material. In this way, the permeability of the membranes will remain relatively unaffected by the presence of gaseous or condensed water in the mask volume. In one embodiment of the invention, one or more of the semi-permeable membranes are made of a hydrophobic material. In one embodiment of the invention, one or more of the semi-permeable membranes comprises a hydrophobic material. In one embodiment of the invention, one or more of the semi-permeable membranes comprises at least one hydrophobic surface, preferably having a surface tension of up to about 35 mN/m determined at 20° C., such as up to about 30 mN/m up to about 25 mN/m.

In one embodiment of the invention, the flow rate of air between the mask volume and the surrounding atmosphere can be adjusted by changing the area of open membrane in the surface of the mask. This can for example be accomplished by the use of small adjustable shutters fitted to the membranes in such a way that a variable area of membrane can be closed off so that no air flow can pass through that area. In one embodiment of the invention, the connections between the mask and the surrounding atmosphere (membranes and/or valves) are restricted in how much they can be closed by the user, so that the oxygen content cannot fall below a specified minimum value. This minimum value can be set at an oxygen concentration between 0 and 21%. In one embodiment of the invention, the mask includes adjustable straps (which can be of an elastic material) which can be fastened around the back of the neck and/or head, so that the mask fits tightly around the nose and mouth of the user. In one embodiment of the invention, the mask is fitted with a soft and/or flexible rim or collar around the edge of the breathing port (the nose/mouth enclosing primary opening), in such a way that the mask fits more tightly around the nose and mouth of the user, thereby directing the entire air flow through the membranes and/or fresh air valve, with a minimum of air leakage between the rim of the breathing port and the face of the user. In one embodiment of the invention, the flexible air chamber of the mask can be removed, thereby facilitating the cleaning of the primary and/or flexible air chamber, as well as allowing flexible air chambers of different sizes to be fitted to the primary air chamber. In one embodiment of the invention, the level of pressure buffering and the mass of rebreathed air can be adjusted by switching between flexible air chambers of different sizes and/or of different materials. In one embodiment of the invention, the primary air chamber and/or the flexible air chamber is fitted with an additional adjustable or non-adjustable valve, the primary purpose of which is to allow condensed water to be drained from the mask. In one embodiment of the invention, a water-absorbing material can be fixed, as well as removed from, inside either the primary or the flexible air chamber or both, thereby allowing liquid or gaseous water to be removed from the mask volume. In this embodiment, it would be possible to replace the water-absorbing material, for example if the material had become completely saturated with water.

According to the invention, it will be possible to install a gas sensor or gas sampling tube in the primary or flexible air chamber, thereby allowing the gas concentrations and pressure levels in the mask to be monitored, for example on a display or screen. This gas sensor could also be connected to an alarm, either separate or as an integral part of the mask, the alarm being able to alert the user if the gas concentrations in the mask reach certain minimum or maximum values. Such a gas sensor could also be connected to a computer, in order to collect the registered values and/or provide feedback to the user of the mask or someone else. Furthermore, it would also be possible to install a regulation system that would allow a computer to control the adjustment of the valves according to a software program and/or the signals provided by a gas sensor in the primary and/or flexible air chamber. Such a sensor could also be connected to a valve or port in the mask, and made in such a way as to open this valve or port if the breathing of the user and/or the gas concentrations in the mask display any erratic or dangerous pattern, thereby allowing a greater flow of fresh air into the mask volume. Furthermore, it would be possible to equip the mask with a pulse oximeter and/or alarm, in such a way that the pulse oximeter could transcutaneously monitor the oxygen saturation of the blood of the user (for example in the earlobe) and set off the alarm if the saturation falls below a specified value. In one embodiment of the invention the facial mask includes a means of removing and replacing the semi-permeable membranes, allowing replacement of (for example) torn or dirty membranes, or changing between different types of membranes with different flow characteristics.

The invention can be produced in a number of sizes and designs, fitting different shapes and sizes of heads, as well as differences in breathing patterns, health conditions and specific physical disorders.

Use of the embodiments of the invention can be from a very short period of time (a few seconds) up to several days or weeks. The user can be at rest, at work, exercising, sleeping, or doing other activities while wearing the mask. The mask can be used either by the user alone, or in collaboration with a doctor or other therapist.

In contrast to the prior art, the present invention is fitted with one or more semi-permeable membranes in the surface of the primary air chamber and/or flexible air chamber, providing another means of gas transport between the mask volume and the surrounding atmosphere, the transport rates of individual gas components depending on the nature of the semi-permeable membrane. Furthermore, some of the embodiments of the mask provide a means for regulating the pressure buffering provided by the flexible air chamber independently of the regulation of the fresh air flow to the user, with both the fresh air valve and the bag valve being connected directly to the primary air chamber, in effect giving a more compact design which is suitable for a mask which can be worn by the user while doing other activities, as well as minimizing the volume of dead space which the mask adds to the physiological dead space of the user (in physiology, dead space is the volume of the air that is inhaled by the body in breathing, but does not take part in gas exchange).

In an aspect the invention comprises a facial breathing mask for regulating the carbon dioxide concentration in inspired air wherein the facial mask comprising a primary air chamber with a primary opening through which a user can breathe, wherein the primary air chamber comprises a semi-permeable membrane separating the primary air chamber and a surrounding atmosphere.

In an aspect the invention comprises a facial breathing mask for regulating the carbon dioxide concentration in inspired air the facial mask comprising an at least partly collapsible air chamber with an opening through which a user can breathe, wherein the at least partly collapsible air chamber comprises a semi-permeable membrane separating the primary air chamber and a surrounding atmosphere, wherein the semi-permeable membrane has an inner-surface facing the chamber and an opposite outer surface facing away from the chamber at least the outer surface is hydrophobic. The outer surface of the semi-permeable membrane has preferably a surface tension of up to about 35 mN/m determined at 20° C., such as up to about 30 mN/m up to about 25 mN/m.

BRIEF DESCRIPTION OF THE DRAWINGS

Referring to the figures, several embodiments of the invention are described below.

FIG. 1 is a perspective drawing of one embodiment of the invention, with two adjustable valves connected to the primary air chamber: a fresh air valve and a valve leading to an expandable bag.

FIG. 2 is a schematic overview of the air flows through the embodiment of the invention shown in FIG. 1.

FIG. 8 is schematic overview of the air flows through the embodiment of the invention pictured in FIG. 5.

DETAILED DESCRIPTION OF THE INVENTION

Figure 3:
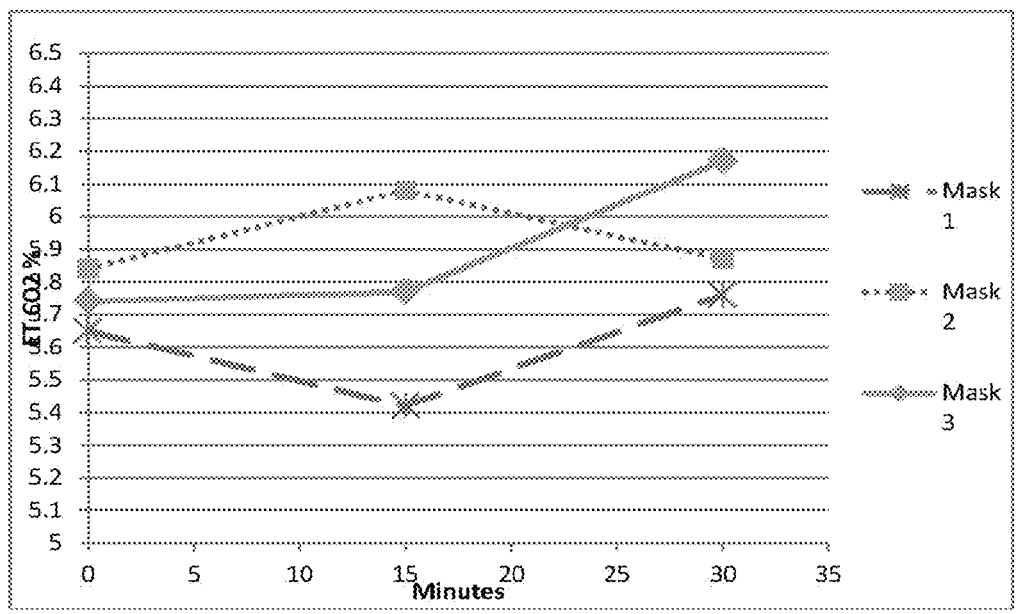
FIG. 3 is a graph of the End Tidal $CO_2$ measurements at the beginning, halfway through, and after 30-minute tests of three masks, Mask 3 corresponding to the embodiment of the invention pictured in FIG. 5.

The embodiment of the invention shown in FIG. 1 and FIG. 2 shows the primary air chamber 2, fitted with two adjustable straps 4 & 6 for fitting around the back of the head and neck respectively, in such a way that the breathing port of the mask can be fixed in place around the nose and mouth of the user. Along the edge of the primary air chamber, a soft and/or flexible rim 8 is fitted, in order to ensure that there is a tight fit between the face of user and the mask. This rim can for example be made of plastic or rubber.

On the front side of the mask (the side furthest from the face of the user), two semi-permeable membranes (3) constitute part of the wall of the primary air chamber, and two short pipes 10 & 12 are fitted, in each of which is fitted an adjustable valve 14 & 16 (shown schematically in FIG. 2). These valves can be of any configuration which allows a stepwise or gradual regulation of the flow through the valve. In this embodiment, the regulation of the valves can be done by adjusting the external knobs 18 & 20, respectively. The upper pipe 10 provides a passage of air between the primary air chamber and the surrounding atmosphere, while the lower pipe 12 provides a passage of air between the primary air chamber and an expandable bag 22. The bag 22 is fitted on the pipe 12 in such a way that there is a tight fit between the two, but making it possible to remove the bag in order to clean it or replace it with another bag of the same or a different size and/or material. In FIG. 2, the flows of air are shown in a schematic manner, referring to the embodiment of the invention shown in FIG. 1. The number 30 on the figure refers to the patient and the number 32 refers to a surrounding atmosphere, exterior to the body of invention.

Figure 5:
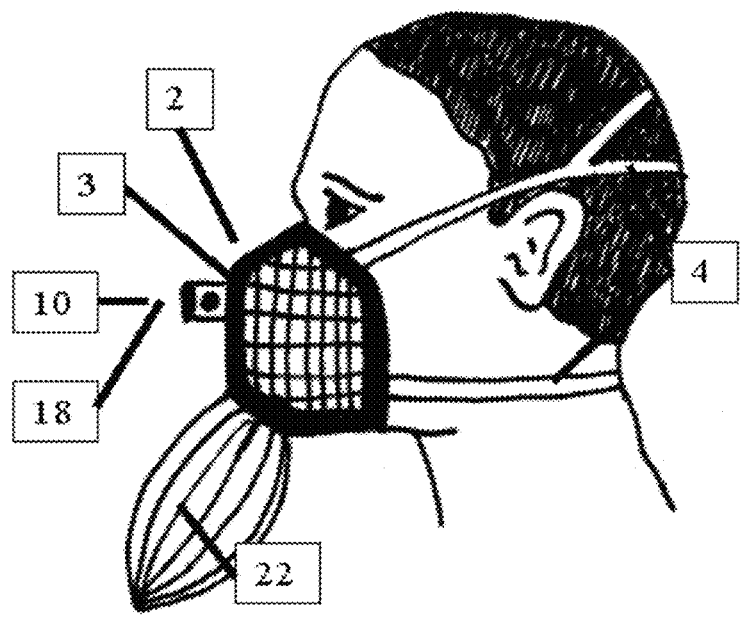
FIG. 5 shows an embodiment of the invention which includes a fresh air valve in the wall of the primary air chamber.

FIG. 5 shows an embodiment of the invention, including a primary air chamber 2 with adjustable straps 4, a semipermeable membrane 3 in the primary air chamber wall, a flexible air chamber 22, a pipe 10 between the primary air chamber and the surrounding atmosphere (this pipe being fitted with a knob 18 for adjusting the valve inside the pipe 10).

Figure 6:
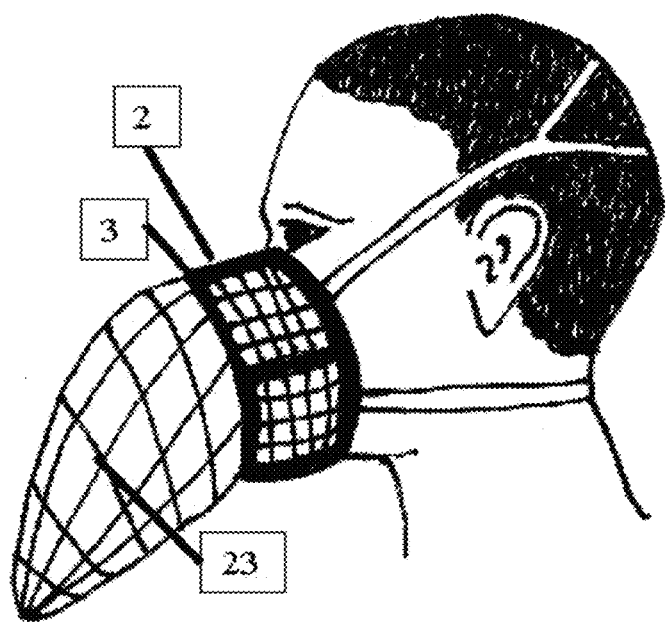
FIG. 6 shows an embodiment of the invention in which the flexible air chamber is attached directly to the primary air chamber (with no pipe or other flow constriction between the two chambers) and in which the wall of the flexible air chamber is made from a semi-permeable material.

FIG. 6 shows an embodiment of the invention in which the flexible air chamber 23 is attached directly to the primary air chamber 2 (with no pipe or other flow constriction between the two chambers). In this embodiment, the wall of the flexible air chamber 23 is furthermore made from a semi-permeable material.

Figure 7:
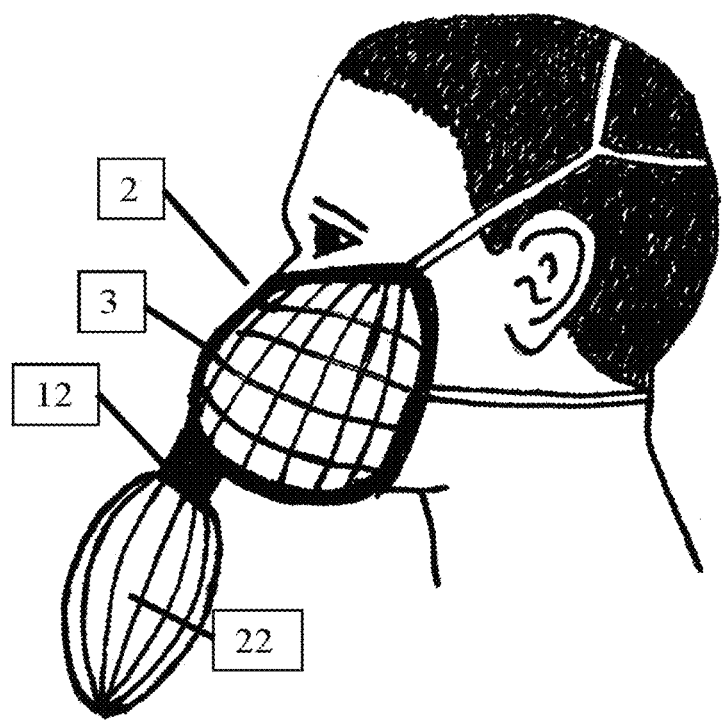
FIG. 7 shows an embodiment of the invention with a primary air chamber with semi-permeable membranes in the chamber wall and a pipe connecting the primary air chamber and the flexible air chamber.

FIG. 7 shows an embodiment of the invention which includes a primary air chamber 2 with a number of semipermeable membranes 3, as well as a pipe 12 connecting the primary air chamber and the flexible air chamber 22.

EXAMPLES

In a series of experiments, a range of different breathing mask designs were tested in use, comparing their capacity for raising the $CO_2$ concentration in the body, without inducing hypoxia. In FIG. 3, the End Tidal $CO_2$ measurements are shown for the user of the three masks, at the beginning, halfway through, and after the 30 minute test.

Mask 1 in FIG. 3 corresponds roughly to one embodiment of U.S. Pat. No. 5,647,345 (described above), being a close-fitting mask without membranes but with a small port between the mask volume and the atmosphere.

Mask 2 in FIG. 3 is similar in having one port and no membranes, but differs from Mask 1 in being fitted with a short pipe leading to a rebreathing bag. This design is similar to the principle of U.S. Pat. No. 4,192,301, UK patent 2378904 and German patent 19912337.

Mask 3 corresponds to the embodiment of the invention shown in FIG. 5, having an adjustable bypass valve between the primary air chamber and the surrounding atmosphere, a rebreathing bag and two hydrophobic PTFE (polytetrafluoroethylene) membranes in the surface of the mask.

It can be seen from the figure, that the membrane-fitted Mask 3 showed the greatest and most unambiguous capacity for raising the $CO_2$ concentration in the body.

None of the masks led to any symptoms of hypoxia, acidosis or any other gas-related discomfort, but in mask 1, the pressure fluctuations in the mask made it necessary to tighten the straps of the mask in order to ensure a tight fit, and the resulting pressure of the mask edges on the face led to some discomfort and soreness.

Compared with mask 2, mask 3 produced much less condensation (two drops vs. approximately 25) in the rebreathing bag, indicating that the membranes had a good capacity for venting off gaseous water from the mask volume.

In another experiment, an embodiment of the mask corresponding to FIG. 1 was tested in use for one hour (after an initial baseline test of breathing without the mask for 15 minutes). Before and after the test, an arterial blood sample was taken from the user, in order to evaluate the effect of the treatment on the blood parameters. The oxygen saturation of the blood was continuously monitored with a pulse oximeter.

Table 1 below shows the data obtained:

TABLE 1

| Blood parameter | Measurement before test | Measurement after test |
| --- | --- | --- |
| Arterial $CO_2$ pressure [kPa] | 5.69 | 6.32 |
| Arterial bicarbonate concentration [mmol/l] | 27.5 | 28.2 |
| pH of arterial blood | 7.426 | 7.393 |

Figure 4:
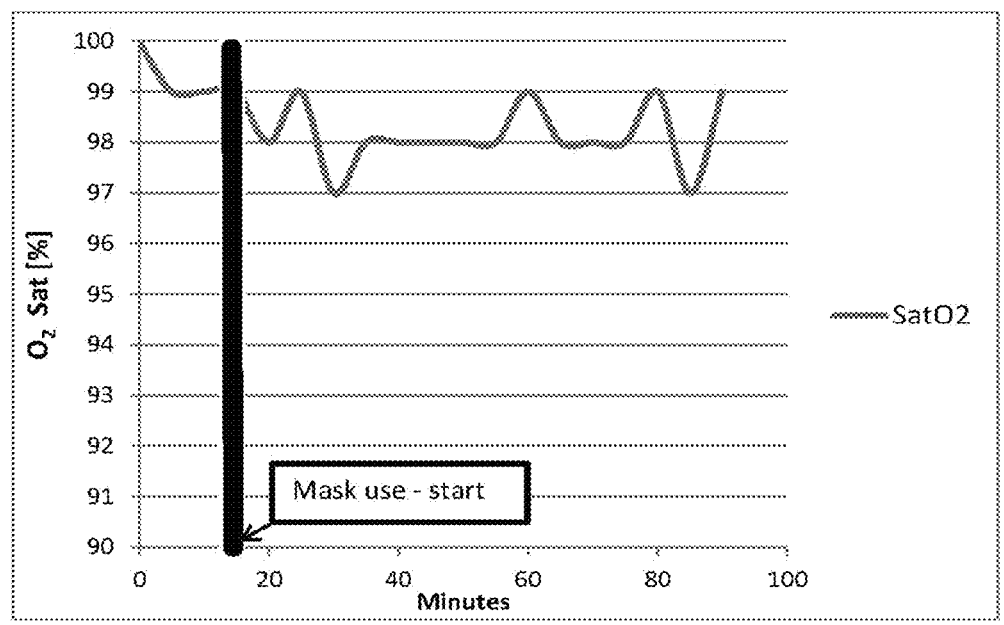
FIG. 4 is a graph of the oxygen saturation during a one hour test of a mask corresponding to the embodiment of the invention pictured in FIG. 5.

During the experiment, the oxygen saturation of the blood fell slightly from the baseline, but still remained at a continually high level, fluctuating between 97 and 99%, as measured by the pulse oximeter (see FIG. 4), thus giving a clear indication that the mask does not lead to hypoxia.

From these data, it can be seen that the mask proved able to raise the $CO_2$ concentration in the body (stored both physically as dissolved gas and chemically in the form of bicarbonate), without incurring a risk of hypoxia. The respiratory acidosis induced proved to be of a relatively low magnitude.

In the present experiment, the test person was not hypocapnic, and so actually experienced hyper-capnia during the experiment. For a chronically hypocapnic patient, however, a measured heightening of the bodily $CO_2$ concentration will induce normocapnia (a physiologically normal $CO_2$ concentration in the body). By maintaining this normocapnic state for longer stretches of time, the compensatory metabolic acidemia of chronically hypocapnic patients can be gradually reversed, thus restoring normal blood gas values.

In a series of further technical tests with the same embodiment of the invention, it was ascertained that:

The CDA mask makes it possible to raise the bodily $CO_2$ concentration to a stable, normocapnic level.

Compared with other mask types, the membranes of the CDA mask facilitated a higher oxygen concentration in the mask at a given $CO_2$ concentration, while also significantly lowering the vapor pressure in the mask volume.

Compared with a fixed increase of the dead space (i.e. a snorkel), a rebreathing bag is more compact and gives a higher increase in the $CO_2$ level.

It is in theory possible for the user of the mask to negate the rise in bodily $CO_2$ concentration, but this seems not to happen in practice unless the user actively focuses on increasing his/her minute ventilation.

According to a MATLAB simulation of the mask flow dynamics, it was found that:

The gas selectivity of the membranes can give an oxygen increase of at least 2 percentage points in the mask volume compared with types of mask without membranes, a difference that will be of clinical significance.

To reach the maximum potential of the membranes, it is essential that the total pressure fluctuations inside the mask volume are limited as much as possible—in practice by ensuring that the connecting pipe between the rebreathing bag and the mask volume has a sufficiently large flow diameter. With low total pressure fluctuations, the selective diffusive will dominate over the non-selective convective flow in the gas exchange between mask volume and atmosphere, thus yielding the maximal gas-selectivity.

Furthermore, a clinical pilot study was undertaken in 2011 at Aarhus University Hospital (Aarhus, Denmark), in which six patients with chronic idiopathic hyperventilation (CIH) were treated with the CDA mask for two hours a day over four weeks, with the following main results:

A statistically significant increase in the bodily $CO_2$ concentration was attained over the treatment period (measured as $P_{CO2}$ and Standard Base Excess)

A statistically significant reduction in CIH symptoms was seen over the treatment period (as measured by the Nijmegen questionnaire).

For all serum electrolytes except chloride, a rise in concentration was seen over the treatment period.

A rise in breath hold tolerance (the time a person can hold his/her breath before feeling the desire to breathe again) over the treatment period—indicating a decrease in the carbon dioxide sensitivity, a sensitivity which may be too high in these patients.

The invention claimed is:

1. A facial breathing mask, suitable for regulating carbon dioxide concentration in inspired air as well as a depth and rate of breathing, said facial mask comprising in combination:

a primary air chamber having a surface and a primary opening in said primary air chamber through which a user can breathe, at least one semi-permeable membrane in the surface of said primary air chamber, separating said primary air chamber and a surrounding atmosphere, wherein a diffusion rate of carbon dioxide through the semi-permeable membrane is lower than a diffusion rate of a different gas through the semi-permeable membrane to thereby retain carbon dioxide within the mask, at least one flexible air chamber in fluid connection with said primary air chamber, said at least one flexible air chamber having a volume which can expand and contract according to a mass of air inside said at least one flexible air chamber, wherein the facial breathing mask is configured to raise carbon dioxide tension in the inspired air.

2. A facial mask according to claim 1, comprising at least one additional opening between the primary air chamber and the surrounding atmosphere, said at least one additional opening comprising one or more adjustable valves, said one or more adjustable valves enabling the rate of gas flow through said at least one additional opening to be varied.

3. A facial mask according to claim 2, in which one or more of said one or more adjustable valves are made in such a way that said one or more of said one or more adjustable valves cannot be adjusted so as to completely block the air flow therethrough.

4. A facial mask according to claim 1, in which a flow connection between the primary air chamber and the at least one flexible air chamber is adjustable in size.

5. A facial mask according to claim 4, in which the flow connection between the primary air chamber and the at least one flexible air chamber is adjustable in size by use of an adjustable valve.

6. A facial mask according to claim 1, in which one or more of said at least one semi-permeable membrane is made of a hydrophobic material.

7. A facial mask according to claim 1, in which the at least one flexible air chamber comprises a bag, which bag can be of an elastic or non-elastic material.

8. A facial mask according to claim 1, in which the at least one flexible air chamber is detachable from the primary air chamber.

9. A facial mask according to claim 1, in which a surface of the at least one flexible air chamber comprises a semi-permeable material.

10. A facial mask according to claim 1, in which an edge of the primary opening is fitted with a flexible rim, said rim facilitating an entirely or partially air-tight fit between the edge of the primary opening and the face of the user.

11. A facial mask according to claim 10, comprising one or more straps for fixing the mask around the user's head, in such a way that it is possible to achieve a tight fit between the rim of the primary opening and the user's face, said rim thereby enclosing the nose and mouth.

12. A facial mask according to claim 1, in which the primary air chamber and/or the at least one flexible air chamber comprises a valve for draining off condensed water.

13. A facial mask according to claim 1, wherein said volume is between 5% and 3000% of a volume of the primary air chamber.

14. A facial mask according to claim 1, comprising a water absorbing material in the primary air chamber or the at least one flexible air chamber, said material being removable from the mask and replaceable.

* * * * *